United States Patent [19]

King

[11] Patent Number: 4,976,946

[45] Date of Patent: Dec. 11, 1990

[54] SEPARATION OF POTASSIUM SALTS

[75] Inventor: Ian R. King, South Wootton, England

[73] Assignee: The Dow Chemical Company, Midland, Mich.

[21] Appl. No.: 477,683

[22] Filed: Feb. 9, 1990

[51] Int. Cl.$^5$ .................... C01D 3/02; C07D 211/72
[52] U.S. Cl. .................................. 423/490; 210/915; 544/242; 546/304; 546/345
[58] Field of Search ............... 546/345, 304; 544/242; 423/490, 181; 210/634, 915; 562/485, 494, 580, 600, 608

[56] References Cited

U.S. PATENT DOCUMENTS

| | | | |
|---|---|---|---|
| 3,761,486 | 9/1973 | McGregor et al. | 546/291 |
| 3,923,822 | 12/1975 | Domenico | 546/345 |
| 4,542,221 | 9/1985 | Jones | 546/304 |
| 4,713,231 | 12/1987 | Campbell et al. | 423/356 |
| 4,746,744 | 5/1988 | Wilson et al. | 546/345 |
| 4,822,887 | 4/1989 | Little et al. | 546/345 |

*Primary Examiner*—Jeffrey E. Russel
*Assistant Examiner*—Brian M. Bolam
*Attorney, Agent, or Firm*—D. Wendell Osborne

[57] ABSTRACT

The potassium salts in aqueous mixtures of potassium fluoride and potassium salts of organic acids are separated and separately recovered by adding a dipolar, aprotic solvent until two liquid phases are present and then separating the phases. The aqueous phase contains the potassium fluoride and the solvent phase contains the potassium salt of an organic acid. Potassium fluoride and potassium 3,5-dichloro-6-fluoro-2-pyridinate, for example, are separately recovered from aqueous mixtures containing both by adding N-methyl-2-pyrrolidinone.

16 Claims, No Drawings

SEPARATION OF POTASSIUM SALTS

BACKGROUND OF THE INVENTION

The present invention relates to a method of separating potassium fluoride from potassium salts of organic acids in aqueous mixtures containing both. The salts can be independently recovered after separation.

Chemical processes involving fluorinated compounds as reactants or products often result in an aqueous product or by-product stream containing essentially, but not necessarily exclusively, potassium fluoride and one or more potassium salts of organic acids. The high value of potassium fluoride as compared with sodium fluoride both as a reactant and as a sales item makes it attractive to develop processes resulting in such mixtures. Examples of processes of this type include processes in which a fluorinated hydrocarbon or heterocyclic compound, such as a fluoropyridine, is made to react with potassium hydroxide to form potassium fluoride and a potassium salt of an hydroxylated compound and processes wherein hydrogen fluoride is employed or formed as a by-product in the presence of an organic acid and is neutralized with aqueous potassium hydroxide. In processes of this type, however, it is important from cost and waste disposal points of view to recover both the potassium fluoride and the potassium salts of organic acids that are present. The potassium fluoride is ideally recovered in a form that will allow for its recycle, alternate use, or sale. The potassium salts of organic acids are ideally recovered in a form suitable for further chemical processing, alternate use, or sale. The development of a process that achieves these ideals would be of considerable commercial value.

SUMMARY OF THE INVENTION

It has now been found that an excellent separation of potassium fluoride and potassium salts of organic acids is achieved when aqueous mixtures containing both are combined with a water-soluble dipolar, aprotic solvent. Surprisingly, when a sufficient amount of the dipolar, aprotic solvent has been added to the aqueous mixture containing potassium fluoride, two liquid phases, one containing most of the water and the potassium fluoride and the other containing most of the dipolar, aprotic solvent and the potassium salts of organic acids, are formed. These phases are readily separable by conventional means and can be further processed to separately recover the potassium fluoride and the potassium salts of organic acids in a desirable form.

The invention includes a process for separately recovering the potassium fluoride and the potassium salts of organic acids present in an aqueous mixture containing both which comprises combining said aqueous mixture with a sufficient amount of dipolar, aprotic solvent to (a) cause two liquid phases to form, one aqueous based and the other dipolar, aprotic solvent based, and (b) contain the potassium salts of organic acids as a solute in the dipolar, aprotic solvent based phase and, thereafter, separating the phases so as to recover the potassium fluoride in the aqueous based phase and to recover the potassium salts of organic acids in the dipolar, aprotic solvent based phase.

The process is especially valuable when applied to chemical processes which produce a potassium salt of an organic acid and generate potassium fluoride as a by-product, such as the hydrolytic replacement of fluoro substituents in hydrocarbons and heterocyclic compounds by means of potassium hydroxide or potassium carbonate.

Dipolar, aprotic solvents of the N,N-dialkylamide type, such as N-methyl-2-pyrrolidinone, N,N-dimethylformamide and N,N-dimethylacetamide, and acetonitrile are preferred solvents. Potassium 4-amino-3,5-dichloro-6-fluoro-2-pyridinate and potassium 3,5-dichloro-6-fluoro-2-pyridinate are preferred potassium salts of organic acids.

DETAILED DESCRIPTION OF THE INVENTION

The process of the present invention is generally effected by combining, with good mixing, a water soluble, dipolar, aprotic solvent and an aqueous mixture containing potassium fluoride and at least one potassium salt of an organic acid. Generally, the first small amount of the solvent added will dissolve and there will be only one liquid phase present. Additional solvent is added until two liquid phases are observed. The two phases are then separated by conventional means, such as by decantation, and are, thereafter, handled independently.

The aqueous phase, which is usually the more dense phase, contains the potassium fluoride. This phase can be used as is or can be further processed. For example, it can be dried to obtain solid potassium fluoride, dispersed in fresh N-methyl-2-pyrrolidinone and dried by distilling out water to obtain a finely divided suspension of potassium fluoride in that solvent, treated with calcium chloride to obtain calcium fluoride as an insoluble salt which can be removed by filtration or centrifugation and sold, or treated by any other known process for such solutions. Recovered anhydrous potassium fluoride can be utilized as a reagent for the exchange of fluoride for chloride in chlorinated hydrocarbons or heterocyclic compounds. For example, it can used to convert pentachloropyridine to 3,5-dichloro-2,4,6-trifluoropyridine or to convert 2,3,5,6-tetrachloropyridine to 3,5-dichloro-2,6-difluoropyridine by known methods.

The organic solvent based phase contains the potassium salts of organic acids present. This phase can be used as is or can be further processed. For example, it can be dried further by distillation of any remaining water to obtain an anhydrous solution suitable for use in many chemical processes, stripped of solvent by distillation to obtain solid potassium salts of organic acids, neutralized with acids to obtain a solution containing the organic acids, or treated by any other known process for such solutions. Potassium salts of organic acids obtained by the process can be used as reagents for synthesis. They can, for example, be alkylated with an alkyl halide, acylated with an acyl halide, phosphorylated with a phosphorochloridate or phosphorochlorothioate or sulfonated with an alkanesulfonyl chloride. The products obtained are useful as insecticides, herbicides, medicinals, and the like.

The process is applicable to aqueous mixtures containing potassium fluoride and one or more salts of organic acids regardless of the source. The mixtures may contain other components, but if they do these components will generally be present as contaminants in either the potassium fluoride or the potassium salts of organic acids separated. Such contaminants can often be removed from the potassium fluoride or organic acid salt solutions obtained in the process or from the recovered salts by conventional means. For example, the aqueous potassium fluoride solution can be extracted with an organic solvent and the potassium salt of an organic acid solution can be extracted with an immiscible organic solvent, such as decane. In many situations the contaminants do not have an adverse effect on the prospective use of the potassium fluoride or organic acid salts obtained in the process and do not need to be removed.

Essentially any water-soluble dipolar, aprotic solvent in which potassium salts of organic acids are soluble can be employed. The process works best with N,N-dialkylamide type dipolar, aprotic solvents, such as N-methyl-2-pyrrolidinone, N,N-dimethylformamide, N,N-dimethylacetamide, 1,3-dimethyl-2-imidazolidinone, and 1,3-dimethyl-3,4,5,6-tetrahydro-2(1H)-pyrimidinone, and with acetonitrile. Other useful solvents include dimethyl sulfoxide, hexamethylphosphoramide, and sulfolane. N-methyl-2-pyrrolidinone, N,N-dimethylformamide, N,N-dimethylacetamide, and acetonitrile are preferred and N-methyl-2-pyrrolidinone is especially preferred.

The amount of dipolar, aprotic solvent required to cause separation of the mixture into two liquid phases is dependent on the relative amount of water and potassium fluoride present, the identity of the dipolar, aprotic solvent, the identity and amount of other solutes present, and the temperature. An appropriate amount can readily be determined experimentally using the guidelines and methods set out herein.

Generally, as the concentration of potassium fluoride in the initial solution is increased, less dipolar, aprotic solvent is required to cause phase separation and the separation becomes more complete. The amount of potassium fluoride expressed as a ratio of potassium fluoride to water, however, should not exceed about 1:0.62, the ratio found in potassium fluoride dihydrate, because at higher concentrations potassium fluoride will sometimes precipitate, forming a third, solid phase. The process will work if the initial solution contains any appreciable amount of potassium fluoride. Solutions containing potassium fluoride to water ratios of about 1:10 to about 1:0.6 generally work best. Solutions having ratios of about 1:4 to about 1:0.7 are often preferred. When solutions having potassium fluoride in excess of a ratio of about 1:1.7 are employed, the temperature is preferably kept above about 40° C. to avoid the formation of solids. If solids are present, they can be removed by filtration, centrifugation, or sedimentation before the liquid phases are separated. The solids are generally potassium fluoride or a hydrate thereof.

Aqueous solutions containing potassium fluoride and potassium salts of organic acids having a potassium fluoride to water ratio outside the specified ranges or different from the optimum value for a specific situation can be readily adjusted to the desired value by adding additional potassium fluoride, adding additional water, or removing water by distillation. The process can, accordingly, be adapted for any aqueous solution containing potassium fluoride and potassium salts of organic acids as major components.

The amount of dipolar, aprotic solvent to be employed in the process must also be sufficient to hold the salts of organic acids in the system in solution during the separation. This amount is variable depending of the dipolar aprotic solvent employed, the identity of the potassium salt of an organic acid present, and the temperature. The minimum amount for any specific situation can be readily determined by a conventional solubility test.

The process of the present invention can be carried out at any temperature between about 0° C. and the boiling point of the mixture. It is best carried out between about 20° C. and about 100° C. It is often preferred to carry out the process above about 41° C., the melting point of potassium fluoride dihydrate. It is also often preferred to carry out the process at temperatures above about 40° C. because the separations appear to improve as the temperature is increased. That is, generally, as the temperature is increased within the best range at least one of the amount of potassium fluoride in the solvent phase, the amount of water in the solvent phase, the amount of potassium salts of organic acids in the aqueous phase, and the amount of dipolar, aprotic solvent in the aqueous phase decreases. Temperatures below about 98° C. are also often preferred for ease in handling. It is, however, at other times preferable to carry out the process at or near ambient temperature in order to eliminate or reduce the cost and inconvenience of heating or cooling.

The process of the present invention appears to be applicable to potassium salts of organic acids in general. Appropriate organic acids include carboxylic acids, such as substituted or unsubstituted benzoic acids and substituted or unsubstituted alkanoic acids: substituted or unsubstituted phenols: substituted or unsubstituted pyridinols: substituted or unsubstituted pyrimidinols: and the like. Specific examples include 2-fluoro-4-cyanophenol, 3-(trifluoromethyl)phenol, 3,5-dichloro-6-fluoro-2-pyridinol, 4-amino-3,5-dichloro-6-fluoro-2-pyridinol, 6-fluoro-2- pyridinol, 5-fluorouracil, 6-fluoro-2-methyl-4-pyrimidinol, butanoic acid, 2-(4-(4-chlorophenoxy)phenoxy)propanoic acid, benzoic acid and 2-methoxy-4-nitrobenzoic acid. Potassium salts of optionally substituted phenols, pyridinols, and pyrimidinols are preferred. It is, of course, necessary that the potassium salt of the organic acid be soluble to some extent in the dipolar, aprotic solvent selected. Generally, salts that are soluble in the selected solvent to the extent of at least 5 percent under the separation conditions are employed. Separation efficiencies of over 90 percent are generally obtainable in various applications of the method; that is, each of the materials separated is recovered in the expected phase to the extent of at least 90 percent.

In one specific application of the invention, the separation of potassium fluoride from potassium 4-amino-3,5-dichloro-6-fluoro-2-pyridinate, a separation efficiency of over 99 percent is achievable employing N-methyl-2-pyrrolidinone or N,N-dimethylformamide as the dipolar, aprotic solvent. This is particularly advantageous because an aqueous mixture of these two salts is obtained in some of the known methods of preparation of the latter compound, such as by the aqueous potassium hydroxide hydrolysis of 4-amino-3,5-dichloro-2,6-difluoropyridine. Equally good results are obtainable with potassium 3,5-dichloro-6-fluoro-2-pyridinate, which is typically prepared in an analogous way from 3,5-dichloro-2,6-difluoropyridine. As a result of the process of the present invention, the potassium fluoride present in such mixtures can be recovered by adding a dipolar, aprotic solvent and separating the two liquid phases that form. The aqueous solution phase containing the potassium fluoride obtained can be used as is or the potassium fluoride present in it can be crystallized or converted to other usable forms. The solvent solution phase containing the potassium pyridinate salt obtained can be utilized as is or can be treated to convert it to other usable forms. Thus, a solid potassium pyridinate salt can be obtained by evaporation of the solvents or a solution of this salt in the dipolar, aprotic solvent containing a reduced amount of water or essentially no water can be obtained by removing water by distillation.

The process of the present invention is especially useful when potassium fluoride and a potassium salt of an organic acid are both present in a system as a result of the the same or different preceding operations. Thus, in the preparation of potassium salts of organic acids, it is often advantageous to avoid removing fluoride ion added or produced in the operations conducted at any stage of the preparation prior to the desired separation. For example, it is possible and often preferable in the preparation of potassium 4-amino-3,5-dichloro-6-fluoro-2-pyridinate from 3,5-dichloro-2,4,6-trifluoropyridine to conduct the ammonation and hydrolysis reactions consecutively without removal of the ammonium fluoride produced in the ammonation. In this situation, sufficient aqueous potassium hydroxide is generally added in the hydrolysis procedure to convert the ammonium fluoride produced in the ammonation procedure to ammonia (which can be removed as a gas by heating) and potassium fluoride, as well as to hydrolyze the 4-amino-3,5-dichloro-2,6-difluoropyridine to potassium 4-amino-3,5-dichloro-6-fluoro-2-pyridinate. The aqueous mixture obtained in the process is subsequently used as a substrate in the process of the present invention.

The following examples are presented to demonstrate or illustrate various aspects of the invention. They should not be construed as limiting.

EXAMPLES

Example 1

Liquid Phases in Potassium Fluoride, Water, and Dipolar, Aprotic Solvent Systems The data required to construct phase diagrams for the title systems was collected by preparing carefully weighed out mixtures of two of the reagents, heating or cooling to the desired temperature by means of a bath, and incrementally adding weighed amounts the third reagent, with stirring and heating or cooling to control the temperature to that desired, until phase separation to two liquid phases took place or, if two phases were initially present, until a single liquid phase formed. The weight of each component at this transition point was recorded.

The following data was collected on the system potassium fluoride:water:N,N-dimethylformamide(DMF) at about 23° C.

| KF, grams | Water, grams | DMF, grams |
| --- | --- | --- |
| 0.1 | 5 | 45 |
| 0.5 | 15 | 35 |
| 1.6 | 23.1 | 35 |
| 5 | 45 | 52 |
| 8 | 55 | 52 |
| 12 | 67 | 52 |
| 24 | 97 | 52 |
| 44 | 144 | 52 |
| 59 | 178 | 52 |
| 15 | 35 | 5 |
| 20 | 35 | 1.4 |

-continued

| KF, grams | Water, grams | DMF, grams |
| --- | --- | --- |
| 22.5 | 27.5 | 0.5 |

The following data was collected on the system potassium fluoride:water:N,N-dimethylacetamide(DMA) at about 23° C.

| KF, grams | Water, grams | DMA, grams |
| --- | --- | --- |
| 0.1 | 6.0 | 62.2 |
| 0.2 | 19.6 | 75.9 |
| 0.7 | 30.9 | 62.2 |
| 3.8 | 53.2 | 62.2 |
| 20 | 208.0 | 197.6 |
| 20 | 167.8 | 136.8 |
| 20 | 114.8 | 64.0 |
| 20 | 82.9 | 24.8 |
| 20 | 60.0 | 8.2 |
| 20 | 52.6 | 4.3 |
| 20 | 37.6 | <0.5 |
| 20 | 25 | <0.2 |

The following data was collected on the system potassium fluoride:water:N-methyl-2-pyrrolidinone(NMP) at about 27° C.

| KF, grams | Water, grams | NMP, grams |
| --- | --- | --- |
| 0.2 | 17.5 | 52.8 |
| 1.0 | 27.2 | 52.8 |
| 2.7 | 41.7 | 52.8 |
| 20 | 217.2 | 215.5 |
| 20 | 149.2 | 106.4 |
| 20 | 110.5 | 56 |
| 20 | 85 | 27 |
| 20 | 64.4 | 9.4 |
| 20 | 41.1 | 1.0 |
| 20 | 30.1 | 0.3 |
| 20 | 25 | 0.1 |

The following data was collected on the system potassium fluoride:water:N-methyl-2-pyrrolidinone(NMP) at about 80° C.

| KF, grams | Water, grams | NMP, grams |
| --- | --- | --- |
| 0.2 | 4.4 | 45.0 |
| 0.2 | 7.7 | 54.2 |
| 0.3 | 5.0 | 68.6 |

Example 2

Potassium Fluoride/Potassium 4-Amino-3,5-dicholoro-6-fluoro-2-pyridinate Separation with N-Methyl-2-pyrrolidinone A 1522.5 grams (g) sample of an aqueous solution containing 9.27 percent potassium fluoride and 17.47 percent potassium 4-amino-3,5-dichloro-6-fluoro-2-pyridinate was diluted with 1065.5 g of N-methyl-2-pyrrolidinone in a temperature controlled vessel. The mixture, which amounted to 2588 g and consisted of two liquid phases, was separated by removing the bottom (aqueous) phase through a bottom drain at about 40° C. The aqueous phase obtained amounted to 311.0 g and contained about 24.0 percent potassium fluoride, 0.29 percent potassium 4-amino-3,5-dichloro-6-fluoro-2-pyridinate and 2.89 percent N-methyl-2-pyrrolidinone. The solvent phase obtained amounted to 2264 g and contained about 2.70 percent potassium fluoride, about 11.6 percent potassium 4-amino-3,5-dichloro-6-fluoro-2-pyridinate, and 39.8 percent water. This corresponds to a greater than 99 percent recovery of the potassium 4-amino-3,5-dichloro-6-fluoro-2-pyridinate in the organic phase and over a 55 percent recovery of the potassium fluoride in the aqueous phase.

The phases from above were recombined and distilled to remove 855 g of liquid, which was about 99 percent water. A mixture consisting of about 1733 g and composed of two aqueous phases remained. The phases were separated as before at about 95° C. The aqueous phase obtained amounted to 256 g and contained about 50.8 percent potassium fluoride, 49.2 percent water, and only traces of potassium 4-amino-3,5-dichloro-6-fluoro-2-pyridinate and N-methyl-2-pyrrolidinone. The solvent phase obtained amounted to 1486 g and contained about 0.1 percent potassium fluoride, about 17.7 percent potassium 4-amino-3,5-dichloro-6-fluoro-2-pyridinate, and 9.2 percent water. This corresponds to a greater than 99 percent recovery of the potassium 4-amino-3,5-dichloro-6-fluoro-2-pyridinate in the organic phase and over a 92 percent recovery of the potassium fluoride in the aqueous phase.

A sample of an aqueous solution containing potassium fluoride and potassium 4-amino-3,5-dichloro-6-fluoro-2-pyridinate was diluted with N-methyl-2-pyrrolidinone in a a reactor equipped with a distillation column and fractionating head. A portion of the volatiles were removed by distillation. The two clear liquid phases remaining were separated at about 80° C. The aqueous phase obtained amounted to 124.6 g and contained about 55°-60 percent potassium fluoride, 216 parts per million (ppm) of potassium 4-amino-3,5-dichloro-6-fluoro-2-pyridinate and 0.11 percent N-methyl-2-pyrrolidinone. The solvent phase obtained amounted to 400.5 g and contained less than about 1 percent potassium fluoride, about 34.6 percent potassium 4-amino-3,5-dichloro-6-fluoro-2-pyridinate, and 6.2 percent water. This corresponds to a greater than 99.9 percent of the potassium 4-amino-3,5-dichloro-6-fluoro-2-pyridinate in the organic phase and about 95 percent of the potassium fluoride in the aqueous phase.

Example 3

Potassium Fluoride/Potassium 4-Amino-3,5-dichloro-6-fluoro-2-pyridinate Separation with N,N-dimethylformamide A 1380 g sample of an aqueous solution containing 11.7 percent potassium fluoride and 23.4 percent potassium 4-amino-3 5-dichloro-6-fluoro-2-pyridinate was diluted with 1137 g of N,N-dimethylformamide in a reactor equipped with a 10 plate column and a fractionating distillation head. The solution was distilled at 66° C. and 24 kiloPascals (kPa) pressure to remove 584 g of distillate which consisted of 88.7 percent water and 11.3 percent N,N-dimethylformamide. The temperature of the residue was adjusted to 55°-60° C. and the two clear liquid phases present were separated. The aqueous phase obtained amounted to 292 g and was found to contain about 45.6 percent potassium fluoride, 81 ppm of potassium 4-amino-3,5-dichloro-6-fluoro-2-pyridinate and 0.2 percent N,N-dimethylformamide. The solvent phase obtained amounted to 1548 g and was found to contain about 0.7 percent potassium fluoride, about 20.9 percent potassium 4-amino-3,5-dichloro-6-fluoro-2-pyridinate, and 9.8 percent water. This corresponds to a greater than 99.9 percent recovery of the potassium 4-amino-3,5-dichloro-6-fluoro-2-pyridinate in the organic phase (less than 0.1 percent in the aqueous phase) and greater than 92 percent recovery of the accounted for potassium fluoride in the aqueous phase (less than 7 percent of that initially present found in the organic phase).

Example 4

Preparation of Potassium 4-Amino-3,5-dichloro-6-fluoro-2-pyridinate and Separation From Potassium Fluoride with N,N-Dimethylformamide.

A solution of 66.0 g (1.0 mole) of 85 percent potassium hydroxide and 29.1 g (0.32 mole) of potassium fluoride in 265.5 g of water was prepared and to this was added 99.5 g (0.5 mole) of 95 percent purity 4-amino-3,5-dichloro-2,6-difluoropyridine. The mixture was heated at reflux (107° C.) with stirring for 4 hours and was then allowed to cool to about 40° C. A 454.4 g portion of N,N-dimethylformamide was added. Two clear liquid layers formed. The layers were separated by decantation at 23° C. The lower layer amounted to 130.9 g and had the approximate composition of 37 percent potassium fluoride, 61 percent water, and 2 percent N,N-dimethylformamide. This amounts to about 91 percent of the potassium fluoride present in the system in the lower layer. The upper layer, which was calculated to amount to about 664 g and to contain about 6.6 g of potassium fluoride, 451 g of N,N-dimethylformamide, 206 g of water, and essentially all of the potassium 4-amino-3,5-dichloro-6-fluoro-2-pyridinate present, was diluted with more N,N-dimethylformamide and distilled until essentially all the water was removed to obtain a dry solution of potassium 4-amino-3,5-dichloro-6-fluoro-2-pyridinate in N,N-dimethylformamide which contained over 95 percent of the amount theoretically possible.

Example 5

Preparation of Potassium 4-Amino-3,5-dichloro-6-fluoro-2-pyridinate and Separation From Potassium Fluoride with N-Methyl-2-pyrrolidinone A mixture of 127.2 g (0.63 mole) of 3,5-dichloro-2,4,6-trifluoropyridine and 127.6 g of water was heated to about 45° C. and then 117.1 g of 32 percent aqueous ammonia was added dropwise with stirring over 46 minutes (min), cooling as necessary to keep the temperature below about 50° C. The mixture was allowed to react another hour at about 45° C., a second hour at about 60° C., and about 30 min at 99°-100° C. The hot, stirring mixture was then treated with 72.7 g of 52 percent aqueous potassium hydroxide over a 20 min period to liberate the ammonia from the ammonium fluoride produced by the ammonation. Heating at about 97°-102° C. was continued for about 4 hours to remove nearly all of the ammonia as a gas. Another 131.1 g of potassium hydroxide was then added with stirring to the hot mixture over a 48 min period and the mixture allowed to react under these conditions for another 2 hours to obtain 591.2 g of an aqueous solution of potassium 4-amino-3,5-dichloro-6-fluoro-2-pyridinate and potassium fluoride. A 409.1 g portion of N-methyl-2-pyrrolidinone was then added causing the mixture to form two liquid layers and the mixture was distilled under reduced pressure until a total of 225.6 g of distillate, which was mostly water, was obtained. Another 268.5 g portion of N-methyl-2-pyrrolidinone was added and another 90.1 g of water removed by distillation. A residue of 963.0 g of a two liquid phase mixture remained. This mixture was heated to about 80° C. and the lower layer removed by decantation. This solidified on cooling and had the approximate composition of potassium fluoride dihydrate. It contained only traces of N-methyl-2-pyrrolidinone and potassium 4-amino-3,5-dichloro-6-fluoro-2-pyridinate, but contained about 99 percent of the potassium fluoride present in the system. The upper layer, which contained about 99 percent of the potassium 4-amino-3,5-dichloro-6-fluoro-2-pyridinate in the system, was further distilled under reduced pressure, taking 129.1 g of distillate, until the water content was about 0.1 percent.

What is claimed is:

1. A process for separately recovering potassium fluoride and a potassium salt of an organic acid from an aqueous mixture containing both, which method comprises combining the aqueous mixture with a sufficient amount of dipolar, aprotic solvent to (a) cause two liquid phases to form, one aqueous based and the other dipolar, aprotic solvent based, and (b) contain the potassium salt of an organic acid as a solute in the dipolar, aprotic solvent based phase, and, thereafter, separating the phases so as to recover the potassium fluoride in the aqueous based phase and to recover the potassium salt of an organic acid in the dipolar, aprotic solvent based phase.

2. A process according to claim 1 wherein the solvent is an N,N-dialkylamide type dipolar, aprotic solvent or acetonitrile.

3. A process according to claim 2 wherein the solvent is N-methyl-2-pyrrolidinone, N,N-dimethylformamide, N,N-dimethylacetamide or acetonitrile.

4. A process according to claim 3 wherein the solvent is N-methyl-2-pyrrolidinone.

5. A process according to claim 1 wherein the organic acid is an optionally substituted phenol, pyridinol, or pyrimidinol.

6. A process according to claim 5 wherein the organic acid is a substituted pyridinol.

7. A process according to claim 6 wherein the substituted pyridinol is 3,5-dichloro-6-fluoro-2-pyridinol.

8. A process according to claim 6 wherein the substituted pyridinol is 4-amino-3,5-dichloro-6-fluoro-pyridinol.

9. A process according to claim 1 wherein the aqueous mixture employed is obtained as a reaction product from the hydrolysis of a fluoro substituted hydrocarbon or heterocyclic compound with aqueous potassium hydroxide or carbonate.

10. A process according to claim 9 wherein the fluoro substituted heterocyclic compound is 3,5-dichloro-2,6-difluoropyridine or 4-amino-3,5-dichloro-2,6-difluoropyridine.

11. A process according to claim 1 wherein the recovered potassium fluoride is subsequently dried as a solid or as a slurry in a dipolar aprotic solvent.

12. A process according to claim 1 wherein the solution of potassium salt of an organic acid in a dipolar, aprotic solvent recovered is subsequently dried by distillation.

13. A process according to claim 1 wherein the aqueous mixture employed has a potassium fluoride to water ratio of between about 1:10 and about 1:0.6.

14. A process according to claim 13 wherein the aqueous mixture employed has a potassium fluoride to water ratio of between about 1:4 and about 1:0.7.

15. A process according to claim 1 wherein the temperature is maintained between about 20° C. and about 100° C.

16. A process according to claim 15 wherein the temperature is maintained between about 40° C. and about 98° C.

* * * * *